US007270739B2

(12) United States Patent
Chen et al.

(10) Patent No.: US 7,270,739 B2
(45) Date of Patent: Sep. 18, 2007

(54) FRACTIONATING AND FURTHER CRACKING A $C_6$ FRACTION FROM A NAPHTHA FEED FOR PROPYLENE GENERATION

(75) Inventors: Tan Jen Chen, Kingwood, TX (US); Brian Erik Henry, Baton Rouge, LA (US); Paul F Keusenkothen, Houston, TX (US); Philip A. Ruziska, Kingwood, TX (US)

(73) Assignee: Exxonmobil Research and Engineering Company, Annandale, NJ (US)

( * ) Notice: Subject to any disclaimer, the term of this patent is extended or adjusted under 35 U.S.C. 154(b) by 475 days.

(21) Appl. No.: 10/760,798

(22) Filed: Jan. 20, 2004

(65) Prior Publication Data

US 2004/0182745 A1    Sep. 23, 2004

Related U.S. Application Data

(60) Provisional application No. 60/451,184, filed on Feb. 28, 2003.

(51) Int. Cl.
*C07C 4/02* (2006.01)
*C07C 4/06* (2006.01)

(52) U.S. Cl. .................. 208/113; 208/75; 208/78; 208/80; 208/92; 585/653; 585/300; 585/302; 585/330

(58) Field of Classification Search ............. 208/113, 208/118, 75, 78, 80, 92; 585/653, 300, 302, 585/330
See application file for complete search history.

(56) References Cited

U.S. PATENT DOCUMENTS

| | | | |
|---|---|---|---|
| 2,426,903 A | 9/1947 | Sweeney | |
| 3,692,667 A | 9/1972 | McKinney et al. | |
| 4,051,013 A | 9/1977 | Strother | 208/78 |
| 4,717,466 A | 1/1988 | Herbst et al. | |
| 5,082,983 A | 1/1992 | Breckenridge et al. | 585/475 |
| 5,087,349 A | 2/1992 | Goelzer et al. | 208/113 |
| 5,264,115 A | 11/1993 | Mauleon et al. | 208/67 |
| 5,358,918 A | 10/1994 | Yukang et al. | 502/67 |
| 5,506,365 A | 4/1996 | Mauleon et al. | 585/329 |
| 5,846,403 A | 12/1998 | Swan et al. | 208/113 |
| 5,888,378 A | 3/1999 | Kowalski | 208/114 |
| 6,069,287 A | 5/2000 | Ladwig et al. | 585/648 |
| 6,080,303 A | 6/2000 | Cao et al. | 208/120.01 |
| 6,090,271 A | 7/2000 | Carpency et al. | 208/113 |
| 6,093,867 A | 7/2000 | Ladwig et al. | 585/648 |
| 6,106,697 A | 8/2000 | Swan et al. | 208/77 |
| 6,118,035 A | 9/2000 | Fung et al. | 585/653 |
| 6,222,087 B1 | 4/2001 | Johnson et al. | 585/651 |
| 6,258,257 B1 | 7/2001 | Swan, III et al. | 208/74 |
| 6,258,990 B1 | 7/2001 | Fung et al. | 585/330 |
| 6,313,366 B1 | 11/2001 | Ladwig et al. | 585/648 |
| 6,315,890 B1 | 11/2001 | Ladwig et al. | 208/67 |
| 6,339,180 B1 | 1/2002 | Ladwig et al. | 585/330 |
| 6,339,181 B1 | 1/2002 | Chen et al. | 585/653 |
| 2001/0025806 A1 | 10/2001 | Steffens et al. | 208/113 |
| 2001/0042700 A1 | 11/2001 | Swan III, et al. | 208/68 |
| 2001/0053868 A1 | 12/2001 | Chester et al. | 585/648 |

FOREIGN PATENT DOCUMENTS

| | | |
|---|---|---|
| BE | 1061116 | 12/2000 |
| DE | 0152356 | 11/1981 |
| DE | 3609653 | 11/1986 |
| EP | 0654523 | 8/1999 |
| EP | 1205530 | 5/2002 |
| EP | 0849347 | 4/2003 |
| FR | 0323297 | 6/1991 |
| JP | 61289049 | 12/1986 |
| WO | WO 00/40672 | 7/2000 |
| WO | WO 01/34727 | 5/2001 |
| WO | WO 01/34729 | 5/2001 |
| WO | WO 01/34730 | 5/2001 |
| WO | WO 01/64763 | 9/2001 |
| WO | WO 01/79383 | 10/2001 |
| WO | WO 01/90278 | 11/2001 |

OTHER PUBLICATIONS

Canadian Journal of Chem. Eng., 63(3), 451-461, 1985, (Reference 6, Queen's University, Kingston, Canada) entitled "Catalytic Cracking and Skeletal Isomerization of n-Hexene on SZM-5 Zeolite."
Niccum, P.K., et al.: "Maxofintm: A Novel FCC Process for Maximizing Light Olefins Using a New Generation ZSM-5 Additive." Annual Meeting Mobil Technology Company National Petroleum Refines Association, Niccum, XX, XX, Mar. 1998, pp. 1-1A, XP002927512 the whole document.
Chinese Journal of Catalysts (Cuihua Zuebao), 11(2), 132-137, 1991, (Reference 4, Dalian Inst. of Chem. Phys., Academy Sinica, China) entitled "Studies on the Cracking of I-Hexene over Pillared Clay Molecular Sieve."
Richard J. Quann, Larry A. Green, Samuel A. Tabak, Frederick J. Krambeck, "Chemistry of Olefin Oligomerzation over ZSM-5 Catalyst," Ind. Eng. Chem. Res. 1988, 27, 565-570, 1988 American Chemical Society.

Primary Examiner—Tam M. Nguyen
(74) Attorney, Agent, or Firm—Jeremy J. Kliebert; Bruce M. Bordelon

(57) ABSTRACT

The present invention relates to a process for selectively producing $C_3$ olefins from a catalytically cracked or thermally cracked naphtha stream by fractionating the naphtha feed to obtain at least a $C_6$ rich fraction and feeding the $C_6$ rich fraction into a reaction stage at a point wherein the residence time of the $C_6$ rich fraction is minimized.

40 Claims, No Drawings

FRACTIONATING AND FURTHER CRACKING A $C_6$ FRACTION FROM A NAPHTHA FEED FOR PROPYLENE GENERATION

CROSS-REFERENCE TO RELATED APPLICATION

This application claims benefit of U.S. provisional patent application Ser. No. 60/451,184 filed Feb. 28, 2003.

FIELD OF THE INVENTION

The present invention relates to a process for selectively producing $C_3$ olefins from a catalytically cracked or thermally cracked naphtha stream by fractionating the naphtha feed to obtain at least a $C_6$ rich fraction and feeding the $C_6$ rich fraction into a reaction stage at a point wherein the residence time of the $C_6$ rich fraction is minimized.

BACKGROUND OF THE INVENTION

The need for low emissions fuels has created an increased demand for light olefins for use in alkylation, oligomerization, MTBE and ETBE synthesis processes. In addition, a low cost supply of light olefins, particularly propylene, continues to be in demand to serve as feedstock for polyolefin, particularly polypropylene production.

Fixed bed processes for light paraffin dehydrogenation have recently attracted renewed interest for increasing olefin production. However, these types of processes typically require relatively large capital investments as well as high operating costs. It is therefore advantageous to increase olefin yield using processes, which require relatively small capital investment. It is particularly advantageous to increase olefin yield in catalytic cracking processes.

European Patent Specifications 490,435-B and 372,632-B and European Patent Application 385,538-A describe processes for converting hydrocarbonaceous feedstocks to olefins and gasoline using fixed or moving beds. The catalysts included ZSM-5 in a matrix, which included a large proportion of alumina.

U.S. Pat. No. 5,069,776 teaches a process for the conversion of a hydrocarbonaceous feedstock by contacting the feedstock with a moving bed of a zeolite catalyst comprising a zeolite with a medium pore diameter of 0.3 to 0.7 nm, at a temperature above about 500° C. and at a residence time less than about 10 seconds. Olefins are produced with relatively little saturated gaseous hydrocarbons being formed. Also, U.S. Pat. No. 3,928,172 to Mobil teaches a process for converting hydrocarbonaceous feedstocks wherein olefins are produced by reacting said feedstock in the presence of a ZSM-5 catalyst.

A problem inherent in producing olefin products using cracking units is that the process depends on a specific catalyst balance to maximize production of light olefins while also achieving high conversion of the 650° F.+ feed components to fuel products. In addition, even if a specific catalyst balance can be maintained to maximize overall olefin production relative to fuels, olefin selectivity is generally low due to undesirable side reactions, such as extensive cracking, isomerization, aromatization and hydrogen transfer reactions. Light saturated gases produced from undesirable side reactions result in increased costs to recover the desirable light olefins. Therefore, it is desirable to maximize olefin production in a process that allows a high degree of control over the selectivity of $C_3$ olefins while producing minimal by-products.

SUMMARY OF THE INVENTION

One embodiment of the present invention is a process for producing increased amounts of propylene from naphtha-boiling-range feedstreams comprising:
(a) fractionating a naphtha-boiling-range feedstream to produce at least a $C_6$-rich fraction and a $C_6$-lean fraction;
(b) injecting at least a portion of said $C_6$-lean fraction into a reaction stage, said reaction stage containing a cracking catalyst comprising at least one molecular sieve having an average pore diameter of less than about 0.7 nm wherein said $C_6$-lean fraction contacts said cracking catalyst under effective cracking conditions thereby resulting in at least a product stream;
(c) injecting at least a portion of said $C_6$-rich fraction into the reaction stage at a place downstream from the $C_6$-lean fraction;
(d) fractionating at least a portion of said product stream of step (b) to produce at least a fraction rich in propylene; and
(e) collecting at least a portion of the fraction rich in propylene.

Another embodiment of the present invention provides a process for producing increased amounts of propylene from naphtha-boiling-range feedstreams comprising:
(a) injecting a naphtha-boiling-range feedstream into a reaction stage, said reaction stage containing a cracking catalyst comprising at least one molecular sieve having an average pore diameter of less than about 0.7 nm, wherein said naphtha-boiling-range feedstream contacts said cracking catalyst under effective cracking conditions thereby resulting in at least a product stream;
(b) fractionating at least a portion of said product stream of step (a) to produce at least a fraction rich in propylene, a $C_6$-rich fraction, and a $C_6$-lean fraction; and
(c) collecting at least a portion of the fraction rich in propylene and the $C_6$-lean fraction and recycling at least a portion of the $C_6$-rich fraction to the reaction stage at a place downstream from the $C_6$-lean fraction.

Another embodiment of the present invention provides a process for producing increased amounts of propylene from naphtha-boiling-range feedstreams comprising:
(a) fractionating a naphtha-boiling-range feedstream to produce at least a $C_6$-rich feed fraction and a $C_6$-lean feed fraction;
(b) conducting at least a portion of said $C_6$-lean feed fraction to a reaction stage, said reaction stage containing a cracking catalyst comprising at least one molecular sieve having an average pore diameter of less than about 0.7 nm wherein said $C_6$-lean feed fraction contacts said cracking catalyst under effective cracking conditions thereby resulting in at least a product stream;
(c) injecting at least a portion of said $C_6$-rich feed fraction into the reaction stage at a point downstream from the $C_6$-lean feed fraction;

(d) fractionating at least a portion of said product stream of step (b) to produce at least a fraction rich in propylene; a $C_6$-rich product fraction, and $C_6$-lean product fraction; and (e) collecting at least a portion of the fraction rich in propylene and $C_6$-lean product fraction and recycling at least a portion of the $C_6$-rich product fraction to the reaction stage at a point downstream from the $C_6$-lean feed fraction.

DETAILED DESCRIPTION OF THE INVENTION

It should be noted that the term "injecting" as used herein is meant to encompass any means known for introducing a stream into a piece of processing equipment. It should also be noted that "$C_6$-rich fraction" as used herein is meant to refer to that fraction containing at least about 50 wt. %, preferably at least about 60 wt. %, and more preferably at least about 70 wt. % of $C_6$ compounds.

The present invention is a process designed to increase propylene yields from a catalytic cracking process unit. Thus, in the practice of the present invention, the reaction stage of the process unit is operated under process conditions effective at maximizing the $C_2$ to $C_4$ olefins (particularly propylene) selectivity. Thus, the present invention relates to a process for selectively producing $C_3$ olefins from naphtha-boiling-range feedstreams. In the practice of the present invention, a naphtha boiling range feedstream is contacted with a cracking catalyst in a reaction stage operated under effective conditions thereby producing at least a product stream. The product stream is then fractionated to produce at least a fraction rich in propylene, a $C_6$-rich fraction, and a $C_6$-lean fraction. At least a portion of the fraction rich in propylene and the $C_6$-lean fraction are recovered while at least a portion of the $C_6$-rich fraction is recycled to the reaction stage. In another embodiment of the instant invention, the naphtha boiling range feedstream is first fractionated into at least a $C_6$-rich fraction and a $C_6$-lean fraction. At least a portion of the $C_6$-lean fraction is injected into the reaction stage wherein it is contacted with a cracking catalyst under effective cracking conditions thereby producing at least a product stream. At least a portion of the $C_6$-rich fraction is fed into the reaction stage at a place downstream from the $C_6$-lean fraction, and at least a fraction rich in propylene is subsequently recovered after fractionation. In yet another embodiment of the instant invention, the naphtha boiling range feedstream is first fractionated into a $C_6$-rich feed fraction and a $C_6$-lean feed fraction. At least a portion of the $C_6$-lean feed fraction is injected into the reaction stage wherein it is contacted with a cracking catalyst under effective cracking conditions thereby producing at least a product stream. At least a portion of the $C_6$-rich feed fraction is fed into the reaction stage at a place downstream from the $C_6$-lean feed fraction. At least a portion of the product stream is then fractionated to produce at least a fraction rich in propylene, a $C_6$-rich product fraction, and a $C_6$-lean product fraction. At least a portion of the $C_6$-rich product fraction is also injected at a point downstream from the $C_6$-lean fraction, as described above.

Feedstreams suitable for use herein are naphtha-boiling-range feedstreams boiling in the range of about 65° F. to about 430° F., preferably from about 65° F. to about 300° F. Non-limiting examples of naphtha-boiling-range feedstreams suitable for use herein include light naphthas or raffinates, containing sufficient amounts of $C_4$-$C_9$ olefins and/or paraffins, $C_4$-$C_9$ fractions from light naphthas or raffinates, catalytic cracked naphtha, coker naphtha, steam cracker pyrolysis gasoline, synthetic chemical streams containing sufficient amounts of $C_4$-$C_9$ olefins and/or paraffins or any other hydrocarbons containing sufficient amounts of $C_4$-$C_9$ olefins and/or paraffins. Feedstreams containing high levels of dienes, sulfur, nitrogen, and oxygenates may be selectively hydrotreated prior to use in the presently disclosed process. However, appropriate feeds with low levels of dienes, sulfur, nitrogen, metal compounds and oxygenates can be processed directly from FCC units, cokers or steam crackers without any pretreatment.

In the practice of the present invention, a naphtha boiling range feedstream as defined above is injected into a reaction stage wherein the naphtha boiling range feedstream contacts a cracking catalyst under effective conditions. The reaction stage can be comprised of one or more fixed bed reactors or reaction zones each of which can comprise one or more catalyst beds of the same or different catalyst. Interstage cooling or heating between reactors, or between catalyst beds in the same reactor, can be employed since cracking reactions are generally exothermic. A portion of the heat generated during cracking can be recovered. Where this heat recovery option is not available, conventional cooling may be performed through cooling utilities. In this manner, optimum reaction temperatures can be more easily maintained.

Catalysts suitable for use in the practice of the present invention are cracking catalysts that are comprised of at least one molecular sieve having an average pore diameter less than about 0.7 nanometers (nm). Molecular sieves suitable for use herein are selected from those materials referred to in the art as zeolites and silicoaluminophosphates (SAPO). It is preferred that the at least one molecular sieve be selected from that class of materials known as zeolites, and more preferred that the zeolite be selected from medium pore zeolites. Medium pore size zeolites that can be used in the practice of the present invention are those described in the "Atlas of Zeolite Structure Types", eds. W. H. Meier and D. H. Olson, Butterworth-Heineman, Third Edition, 1992, which is hereby incorporated by reference. Medium pore size zeolites generally have an average pore diameter less than about 0.7 nm, typically from about 0.5 nm, to about 0.7 nm and include for example, MFI, MFS, MEL, MTW, EUO, MTT, HEU, FER, and TON structure type zeolites (IUPAC Commission of Zeolite Nomenclature). Non-limiting examples of such medium pore size zeolites, include ZSM-5, ZSM-12, ZSM-22, ZSM-23, ZSM-34, ZSM-35, ZSM-38, ZSM-48, ZSM-50, silicalite, and silicalite 2. The most preferred zeolite cracking catalyst used in the presently disclosed process is ZSM-5, which is described in U.S. Pat. Nos. 3,702,886 and 3,770,614. ZSM-11 is described in U.S. Pat. No. 3,709,979; ZSM-12 in U.S. Pat. No. 3,832,449; ZSM-21 and ZSM-38 in U.S. Pat. No. 3,948,758; ZSM-23 in U.S. Pat. No. 4,076,842; and ZSM-35 in U.S. Pat. No. 4,016,245. All of the above patents are incorporated herein by reference. The pore diameter, sometimes referred to herein as "effective pore diameter", can be measured using standard adsorption techniques and hydrocarbonaceous compounds of known minimum kinetic diameters. See Breck, Zeolite Molecular Sieves, 1974 and Anderson et al., J. Catalysis 58, 114 (1979), both of which are incorporated herein by reference.

As mentioned above, molecular sieves suitable for use herein also include that class of materials generally known as silicoaluminophosphates (SAPO), such as, for example, SAPO-11, SAPO-34, SAPO-41, and SAPO-42, which are described in U.S. Pat. No. 4,440,871. Other suitable molecular sieves can be selected from chromosilicates; gallium silicates; iron silicates; aluminum phosphates (ALPO), such as ALPO-11 described in U.S. Pat. No. 4,310,440; titanium aluminosilicates (TASO), such as TASO-45 described in EP-A No. 229,295; boron silicates, described in U.S. Pat. No. 4,254,297; titanium aluminophosphates (TAPO), such as TAPO-11 described in U.S. Pat. No. 4,500,651; and iron aluminosilicates.

The cracking catalyst comprising at least one molecular sieve is also meant to encompass "crystalline admixtures" which are thought to be the result of faults occurring within the crystal or crystalline area during the synthesis of the zeolites. Examples of crystalline admixtures of ZSM-5 and ZSM-11 are disclosed in U.S. Pat. No. 4,229,424 which is incorporated herein by reference. The crystalline admixtures are themselves medium pore size zeolites and are not to be confused with physical admixtures of zeolites in which distinct crystals of crystallites of different zeolites are physically present in the same catalyst composite or hydrothermal reaction mixtures.

The cracking catalysts used in the present invention are typically held together with an inorganic oxide matrix component. The inorganic oxide matrix can be made from an inorganic oxide sol or gel which is dried to "glue" the catalyst components together. Preferably, the inorganic oxide matrix is not catalytically active and will be comprised of oxides of silicon and aluminum. It is also preferred that separate alumina phases be incorporated into the inorganic oxide matrix. Species of aluminum oxyhydroxides-g-alumina, boehmite, diaspore, and transitional aluminas such as a-alumina, b-alumina, g-alumina, d-alumina, c-alumina, k-alumina, and r-alumina can be employed. Preferably, the alumina species is an aluminum trihydroxide such as gibbsite, bayerite, nordstrandite, or doyelite. The matrix material may also contain phosphorous or aluminum phosphate.

As mentioned above, the naphtha boiling range feedstream contacts the above-defined cracking catalyst under effective cracking conditions. Effective cracking conditions as used herein will be considered those conditions selected to achieve the desired boiling point conversion of the feed and include temperatures from about 500° C. to about 700° C., preferably from about 525° C. to about 650° C.

The contacting of the naphtha boiling range feedstream with the cracking catalyst produces at least a product stream. At least a portion of this product stream, preferably substantially all, of the product stream from the reaction stage is sent to a fractionation stage where various products are recovered, particularly a $C_3$-rich, i.e. propylene rich, fraction, a $C_6$-rich fraction, a $C_6$-lean fraction, and optionally a $C_4$-rich fraction. The $C_3$ fraction and the $C_4$ fraction will typically be rich in olefins, and at least a portion, preferably substantially all, of the $C_3$ (propylene)-rich fraction can then be collected. In the practice of the present invention, at least a portion, preferably substantially all, of the $C_6$-rich fraction is recycled and injected into the reaction stage at a point downstream from the injection of the naphtha boiling range feedstream to increase the yield of propylene. It is preferred that the $C_6$-rich fraction be injected into the reaction stage at a point downstream from the naphtha boiling range feedstream at a point selected in the reaction stage wherein the liquid hourly space velocity of the $C_6$-rich fraction is greater than about 10 $hr^{-1}$, preferably greater than about 20 $hr^{-1}$, more preferably greater than about 40 $hr^{-1}$, and most preferably greater than about 60 $hr^{-1}$.

As stated above, in one embodiment of the instant invention, a naphtha boiling range feedstream is fractionated into at least a $C_6$-rich fraction and a $C_6$-lean fraction. At least a portion, preferably substantially all, of the $C_6$-lean fraction is introduced or injected into the reaction stage wherein it contacts a cracking catalyst as defined above under conditions as defined above thereby producing at least a product stream. At least a portion, preferably substantially all, of the $C_6$-rich fraction is injected into the reaction stage at a point downstream from the $C_6$-lean fraction. The injection of the $C_6$-rich fraction is selected using the above criteria. At least a portion, preferably substantially all, of the product stream is fractionated to produce at least a fraction rich in propylene. At least a portion, preferably substantially all of the fraction rich in propylene is collected.

In yet another embodiment of the present invention, a naphtha boiling range feedstream is fractionated into at least a $C_6$-rich feed fraction and a $C_6$-lean feed fraction. At least a portion, preferably substantially all, of the $C_6$-lean feed fraction is introduced or injected into the reaction stage wherein it contacts a cracking catalyst as defined above under conditions as defined above thereby producing at least a product stream. At least a portion, preferably substantially all, of the $C_6$-rich feed fraction is injected into the reaction stage at a point downstream from the $C_6$-lean feed fraction. The injection of the $C_6$-rich feed fraction is selected using the above criteria. At least a portion, preferably substantially all, of the product stream is fractionated to produce at least a fraction rich in propylene, a $C_6$-rich product fraction, a $C_6$-lean product fraction. At least a portion, preferably substantially all of the fraction rich in propylene is collected, and at least a portion, preferably substantially all, the $C_6$-rich product fraction is recycled and injected into the reaction stage at a point downstream from the $C_6$-lean feed fraction. The injection of the $C_6$-rich product fraction is selected using the above-described criteria. It should be noted that it is contemplated that in this embodiment, the $C_6$-rich feed fraction and the $C_6$-rich product fraction can be injected into the reaction stage at the same or different points or places.

EXAMPLES

The following examples will illustrate the improved effectiveness of the present invention, but is not meant to limit the present invention in any fashion.

Example 1

A light cat naphtha was distilled into five different fractions to study feedstock effects in naphtha cracking. The distillation was performed according to the ASTM specification for distillation of naphtha, ASTM D-86. The results of the feedstock component properties of the distilled light cat naphtha are given in Table 1.

TABLE 1

FEED COMPONENT PROPERTIES

| Feed % of Feed | IBP-130 | 130-150 | 150-170 | 170-190 | 190+ | ***LCN*** Wt. Avg. | Actual |
|---|---|---|---|---|---|---|---|
| Feed | 33.1 | 14.3 | 11.9 | 7.3 | 33.4 | Wt. Avg. | Actual |
| Olefins, Wt. % | | | | | | | |
| C5 | 62.4 | 9.2 | 0.3 | 0.0 | 0.0 | 22.0 | 26.2 |
| C6 | 4.4 | 49.0 | 48.4 | 20.8 | 0.6 | 16.0 | 15.8 |
| C7 | 0.1 | 5.2 | 14.3 | 30.5 | 22.0 | 12.1 | 10.6 |
| C8 | 0.0 | 0.0 | 0.0 | 0.0 | 5.4 | 1.8 | 1.3 |
| C9 | 0.0 | 0.0 | 0.0 | 0.0 | 1.2 | 0.4 | 0.1 |
| C10 | 0.0 | 0.0 | 0.0 | 0.0 | 0.1 | 0.0 | 0.0 |
| C11 | 0.0 | 0.0 | 0.0 | 0.0 | 0.0 | 0.0 | 0.0 |
| C12 | 0.0 | 0.0 | 0.0 | 0.0 | 0.0 | 0.0 | 0.0 |
| Total, % | 66.9 | 63.5 | 63.0 | 51.3 | 29.4 | 52.3 | 54.0 |

LCN distilled into five cuts to study feedstock effects in naphtha cracking
IBP-130° F. cut olefins mostly pentenes
130-150/150-170° F. cut olefins mostly hexenes
190° F.+ mostly heptenes

Example 2

A series of tests in a small bench reactor were conducted on the various boiling fractions of the light cat naphtha. All tests were conducted at 575° C., 72 hr$^1$ WHSV over a fixed bed of 0.3 g of ZSM-5 medium-pore zeolite catalyst. Prior to the cracking tests, the ZSM-5 catalyst was aged by steaming it with 100% steam at 816° C. and 1 atmosphere for 16 hours.

The yields of key products from these series of tests are given in Table 2.

TABLE 2

OLEFINSMAX IN LCN CRACKING

| Feed | IBP-130 | 130-150 | 150-170 | 170-190 | 190+ | ***LCN*** Wt. Avg. | Actual |
|---|---|---|---|---|---|---|---|
| C4-Conv., Wt % | 22.4 | 41.4 | 45.0 | 39.9 | 32.3 | 32.3 | 32.8 |
| Key Yields, Wt % | | | | | | | |
| Ethylene | 3.3 | 3.0 | 3.5 | 2.2 | 2.6 | 3.0 | 2.7 |
| Propylene | 10.8 | 27.5 | 27.8 | 21.0 | 15.4 | 17.4 | 16.9 |
| Butylene | 7.6 | 10.0 | 12.4 | 15.5 | 12.2 | 10.6 | 11.6 |
| Lt Sats | 0.8 | 0.9 | 1.4 | 1.1 | 2.1 | 1.3 | 1.7 |
| Propane | 0.1 | 0.4 | 0.5 | 0.4 | 0.4 | 0.3 | 0.4 |
| C3=/C4-Sel | 48.2 | 66.4 | 61.8 | 52.6 | 47.7 | 53.9 | 51.5 |

C6 cuts (130-150° F. and 150-170° F.) show the highest propylene yield with OlefinsMax cracking catalyst The effluent stream of the reactor was analyzed by on-line gas chromatography ("GC"). A column having a length of 60 m packed with fused silica was used for the analysis. The GC used was a dual FID Hewlett-Packard Model 5880.

Example 3

In addition to ZSM-5, the various boiling fractions of the light cat naphtha were also tested with a SAPO-11 catalyst. In the case of SAPO-11, the zeolite was tested fresh. Otherwise, the procedure used in the experiments with SAPO-11 was nominally identical to the experiments with ZSM-5. The results are given in Table 3.

TABLE 3

SAPO-11 IN LCN CRACKING

| Feed | IBP-130 | 130-150 | 150-170 | 170-190 | 190+ | ***LCN*** Wt. Avg. | Actual |
|---|---|---|---|---|---|---|---|
| C4-Conv., Wt % | 17.3 | 41.4 | 33.0 | 30.2 | 24.6 | 26.0 | 26.5 |
| Key Yields, Wt % | | | | | | | |
| Ethylene | 3.7 | 1.5 | 1.1 | 0.9 | 0.9 | 1.9 | 1.9 |
| Propylene | 10.5 | 35.8 | 26.5 | 17.0 | 17.0 | 16.4 | 15.2 |
| Butylene | 2.6 | 3.3 | 4.4 | 11.0 | 11.0 | 6.6 | 7.4 |
| Lt Sats | 0.5 | 0.9 | 1.0 | 1.2 | 1.2 | 1.0 | 2.1 |
| Propane | 0.1 | 0.3 | 0.2 | 0.3 | 0.3 | 0.2 | 0.3 |
| C3=/C4-Sel | 60.7 | 86.5 | 80.3 | 56.3 | 56.3 | 63.1 | 57.4 |

C6 cuts (130-150° F. and 150-170° F.) also show the highest propylene yield with SAPO-11

The invention claimed is:

1. A process for producing increased amounts of propylene from naphtha-boiling-range feedstreams comprising:
   (a) fractionating a naphtha-boiling-range feedstream to produce at least a $C_6$-rich fraction and a $C_6$-lean fraction, wherein the $C_6$-rich fraction contains at least 50 wt % $C_6$ compounds;
   (b) injecting at least a portion of said $C_6$-lean fraction into a reaction stage, said reaction stage containing a cracking catalyst comprising at least one molecular sieve having an average pore diameter of less than about 0.7 nm wherein said $C_6$-lean fraction contacts said cracking catalyst under effective cracking conditions thereby resulting in at least a product stream;
   (c) injecting at least a portion of said $C_6$-rich fraction into the reaction stage at a place downstream from the $C_6$-lean fraction;
   (d) fractionating at least a portion of said product stream of step (b) to produce at least a fraction rich in propylene; and
   (e) collecting at least a portion of the fraction rich in propylene.

2. The process of claim 1 wherein the at least one molecular sieve is selected from zeolites and silicoaluminophosphates.

3. The process of claim 2 wherein the at least one molecular sieve is a medium-pore zeolite.

4. The process of claim 3 wherein the medium-pore zeolite is selected from the group consisting of ZSM-5, ZSM-11, ZSM-12, ZSM-22, ZSM-23, ZSM-48, and ZSM-50.

5. The process of claim 2 wherein the silicoaluminophosphates is selected from the group consisting of SAPO-11, SAPO-34, SAPO-41, and SAPO-42.

6. The process of claim 1 wherein the propylene rich fraction has a propylene concentration greater than about 60 wt %.

7. The process of claim 1 wherein said effective cracking conditions in include temperatures from about 500° C. to about 700° C.

8. The process according to claim 1 wherein said molecular sieve is selected from chromosilicates, gallium silicates, iron silicates, aluminum phosphates (ALPO), titanium aluminosilicates (TASO), boron silicates, titanium aluminophosphates (TAPO), and iron aluminosilicates.

9. The process of claim 1 wherein said cracking catalyst further comprises an inorganic oxide matrix component.

10. The process of claim 9 wherein said inorganic oxide matrix component is not catalytically active and is selected from oxides of silicon and aluminum.

11. The process of claim 1 wherein the at least a portion of said $C_6$-rich fraction is injected into the reaction stage at a place downstream from the $C_6$-lean fraction wherein the liquid hourly space velocity of the $C_6$-rich fraction is greater than about 10 $hr^{-1}$.

12. The process of claim 1 wherein said reaction stage is comprised of one or more fixed bed reactors or reaction zones each of which comprises one or more catalyst beds of the same or different cracking catalyst.

13. The process of claim 12 wherein interstage cooling or heating between reactors, or between catalyst beds in the same reactor, is employed in order to maintain optimum reaction temperatures.

14. A process for producing increased amounts of propylene from naphtha-boiling-range feedstreams comprising:
   (a) injecting a naphtha-boiling-range feedstream into a reaction stage, said reaction stage containing a cracking catalyst comprising at least one molecular sieve having an average pore diameter of less than about 0.7 nm, wherein said naphtha-boiling-range feedstream contacts said cracking catalyst under effective cracking conditions thereby resulting in at least a product stream;
   (b) fractionating at least a portion of said product stream of step (a) to produce at least a fraction rich in propylene, a $C_6$-rich fraction, and a $C_6$-lean fraction, wherein the $C_6$-rich fraction contains at least 50 wt % $C_6$ compounds; and
   (c) collecting at least a portion of the fraction rich in propylene and the $C_6$-lean fraction and recycling at least a portion of the $C_6$-rich fraction to the reaction stage.

15. The process of claim 14 wherein the at least one molecular sieve is selected from zeolites and silicoaluminophosphates.

16. The process of claim 15 wherein the at least one molecular sieve is a medium-pore zeolite.

17. The process of claim 16 wherein the medium-pore zeolite is selected from the group consisting of ZSM-5, ZSM-11, ZSM-12, ZSM-22, ZSM-23, ZSM-48, and ZSM-50.

18. The process of claim 15 wherein the silicoaluminophosphates is selected from the group consisting of SAPO-11, SAPO-34, SAPO-41, and SAPO-42.

19. The process of claim 14 wherein the propylene rich fraction has a propylene concentration greater than about 60 wt %.

20. The process of claim 14 wherein said effective cracking conditions in include temperatures from about 500° C. to about 700° C.

21. The process according to claim 14 wherein said molecular sieve is selected from chromosilicates, gallium silicates, iron silicates, aluminum phosphates (ALPO), titanium aluminosilicates (TASO), boron silicates, titanium aluminophosphates (TAPO), and iron aluminosiprocess of claim 15 wherein said cracking catalyst further comprises an inorganic oxide matrix component.

22. The process of claim 14 wherein said cracking catalyst further comprises an inorganic oxide matrix component.

23. The process of claim 22 wherein said inorganic oxide matrix component is not catalytically active and is selected from oxides of silicon and aluminum.

24. The process of claim 14 wherein the at least a portion of said $C_6$-rich fraction is injected into the reaction stage at a place downstream from the $C_6$-lean fraction wherein the liquid hourly space velocity of the $C_6$-rich fraction is greater than about 10 $hr^{-1}$.

25. The process of claim 14 wherein said reaction stage is comprised of one or more fixed bed reactors or reaction zones each of which comprises one or more catalyst beds of the same or different cracking catalyst.

26. The process of claim 25 wherein interstage cooling or heating between reactors, or between catalyst beds in the same reactor, is employed in order to maintain optimum reaction temperatures.

27. A process for producing increased amounts of propylene from naphtha-boiling-range feedstreams comprising:
   (a) fractionating a naphtha-boiling-range feedstream to produce at least a $C_6$ feed fraction, wherein the $C_6$-rich feed fraction contains at least 50 wt % $C_6$ compounds and a $C_6$-lean feed fraction;
   (b) conducting at least a portion of said $C_6$-lean feed fraction to a reaction stage, said reaction stage containing a cracking catalyst comprising at least one molecular sieve having an average pore diameter of less than about 0.7 nm wherein said $C_6$-lean feed fraction contacts said cracking catalyst under effective cracking conditions thereby resulting in at least a product stream;
   (c) injecting at least a portion of said $C_6$-rich feed fraction into the reaction stage at a point downstream from the $C_6$-lean feed fraction;
   (d) fractionating at least a portion of said product stream of step (b) to produce at least a fraction rich in propylene; a $C_6$-rich product fraction, and $C_6$-lean product fraction, wherein the $C_6$-rich product fraction contains at least 50 wt % $C_6$ compounds; and
   (e) collecting at least a portion of the fraction rich in propylene and $C_6$-lean product fraction and recycling at least a portion of the $C_6$-rich product fraction to the reaction stage at a point downstream from the $C_6$-lean feed fraction.

28. The process of claim 27 wherein the at least one molecular sieve is selected from zeolites and silicoaluminophosphates.

29. The process of claim 28 wherein the at least one molecular sieve is a medium-pore zeolite.

30. The process of claim 29 wherein the medium-pore zeolite is selected from the group consisting of ZSM-5, ZSM-11, ZSM-12, ZSM-22, ZSM-23, ZSM-48, and ZSM-50.

31. The process of claim 28 wherein the silicoaluminophosphates is selected from the group consisting of SAPO-11, SAPO-34, SAPO-41, and SAPO-42.

32. The process of claim 27 wherein the propylene rich fraction has a propylene concentration greater than about 60 wt %.

33. The process of claim 27 wherein said effective conditions in the reaction zone include temperatures from about 500° C. to about 700° C.

34. The process according to claim 27 wherein said molecular sieve comprises about 10 wt. % to about 50 wt. % of the total fluidized catalyst composition.

35. The process according to claim 27 wherein said molecular sieve is selected from chromosilicates, gallium silicates, iron silicates, aluminum phosphates (ALPO), titanium aluminosilicates (TASO), boron silicates, titanium aluminophosphates (TAPO), and iron aluminosilicates.

36. The process of claim 27 wherein said cracking catalyst further comprise an inorganic oxide matrix component.

37. The process of claim 36 wherein said inorganic oxide matrix component is not catalytically active and is selected from oxides of silicon and aluminum.

38. The process of claim 27 wherein the at least a portion of said $C_6$-rich fraction is injected into the reaction stage at a place downstream from the $C_6$-lean fraction wherein the liquid hourly space velocity of the $C_6$-rich fraction is greater than about 10 $hr^{-1}$.

39. The process of claim 27 wherein said reaction stage is comprised of one or more fixed bed reactors or reaction zones each of which comprises one or more catalyst beds of the same or different cracking catalyst.

40. The process of claim 39 wherein interstage cooling or heating between reactors, or between catalyst beds in the same reactor, is employed in order to maintain optimum reaction temperatures.

* * * * *